US012335394B2

(12) United States Patent
Miettinen et al.

(10) Patent No.: US 12,335,394 B2
(45) Date of Patent: Jun. 17, 2025

(54) ANONYMOUS DISTRIBUTED CONTACT TRACING AND VERIFICATION SYSTEM

(71) Applicant: Technische Universitaet Darmstadt, Darmstadt (DE)

(72) Inventors: Markus Miettinen, Ober-Ramstadt (DE); Duc Thien Nguyen, Darmstadt (DE); Ahmad-Reza Sadeghi, Seeheim-Jugenheim (DE)

(73) Assignee: Technische Universitaet Darmstadt, Darmstadt (DE)

( * ) Notice: Subject to any disclaimer, the term of this patent is extended or adjusted under 35 U.S.C. 154(b) by 575 days.

(21) Appl. No.: 17/444,090

(22) Filed: Jul. 30, 2021

(65) Prior Publication Data
US 2022/0051808 A1    Feb. 17, 2022

Related U.S. Application Data

(60) Provisional application No. 62/706,095, filed on Jul. 31, 2020.

(51) Int. Cl.
| | |
|---|---|
| *H04L 9/32* | (2006.01) |
| *G16H 50/80* | (2018.01) |
| *H04W 4/021* | (2018.01) |
| *H04W 4/029* | (2018.01) |
| *H04W 4/80* | (2018.01) |
| *H04W 12/64* | (2021.01) |

(52) U.S. Cl.
CPC ........... *H04L 9/3213* (2013.01); *G16H 50/80* (2018.01); *H04W 4/021* (2013.01); *H04W 4/029* (2018.02); *H04W 4/80* (2018.02); *H04W 12/64* (2021.01)

(58) Field of Classification Search
None
See application file for complete search history.

(56) References Cited

U.S. PATENT DOCUMENTS

| | | | | |
|---|---|---|---|---|
| 11,411,715 | B2* | 8/2022 | Kim | ........................ H04L 9/0833 |
| 11,481,768 | B2* | 10/2022 | Heyner | ............... G06Q 20/3825 |
| 2014/0325227 | A1* | 10/2014 | Brown | ................... H04L 9/3252 |
| | | | | 713/171 |

(Continued)

FOREIGN PATENT DOCUMENTS

| | | | | |
|---|---|---|---|---|
| CA | 3090703 A1 | * | 9/2019 | .............. G06F 13/20 |
| CN | 1964257 A | * | 5/2007 | ........... H04L 9/0637 |

(Continued)

OTHER PUBLICATIONS

Decentralized Privacy-Preserving Proximity Tracing; EPFL : Prof. Carmela Troncoso, Prof. Mathias Payer; May 2020. (Year: 2020).*

(Continued)

*Primary Examiner* — Neha Patel
*Assistant Examiner* — Jahed Ali
(74) *Attorney, Agent, or Firm* — Ziolkowski Patent Solutions Group, SC

(57) ABSTRACT

An automated contact tracing system for anonymously identifying contacts between users includes at least a tracing server; and more than one mobile device or wearable of a user comprising means for short-range proximity communication and means for carrying out a computer program for generating Encounter-Tokens, when one user spent a pre-defined amount of time in a pre-defined proximity range of another user.

16 Claims, 3 Drawing Sheets

(56) References Cited

U.S. PATENT DOCUMENTS

| | | | | |
|---|---|---|---|---|
| 2017/0255937 | A1* | 9/2017 | Maddukuri | G06Q 20/3674 |
| 2017/0352119 | A1* | 12/2017 | Pittman | G16H 50/80 |
| 2019/0089532 | A1* | 3/2019 | Lambert | H04L 63/0853 |
| 2019/0230503 | A1* | 7/2019 | Circosta | H04W 12/50 |
| 2021/0044965 | A1* | 2/2021 | Nambisan | H04W 12/63 |
| 2021/0184869 | A1* | 6/2021 | Trere | H04L 9/0844 |
| 2021/0367771 | A1* | 11/2021 | Gray | H04L 9/0894 |
| 2022/0014357 | A1* | 1/2022 | Jones | H04L 9/14 |

FOREIGN PATENT DOCUMENTS

| | | | | |
|---|---|---|---|---|
| CN | 105940391 A | * | 9/2016 | G06F 16/9535 |
| WO | WO-2010099488 A1 | * | 9/2010 | G06F 19/327 |

OTHER PUBLICATIONS

Decentralized Privacy-Preserving Proximity Tracing; EPFL : Prof. Carmela Troncoso, Prof. Mathias Payer; May 2020. (Year: 2020) (Year: 2020).*

Privacy-Preserving Contact Tracing ; Apple and Google; Web page https://www.apple.com/covid19/contacttracing; Apr. 10, 2020; retrieved from Internet Archive Wayback Machine https://web.archive.org/web/20200410173003/https://www.apple.com/covid19/contacttracing on Jul. 21, 2021.

Exposure Notification Bluetooth® Specification; Apple Inc. and Google LLC; Apr. 2020 [retrieved on Jul. 21, 2021]; retrieved from the Internet: https://covid19-static.cdn-apple.com/applications/covid19/current/static/contact-tracing/pdf/ExposureNotification-BluetoothSpecificationv1.2.pdf?1.

Exposure Notification Cryptography Specification; Apple Inc. and Google LLC; Apr. 2020 [retrieved on Jul. 21, 2021]; retrieved from the Internet: https://covid19-static.cdn-apple.com/applications/covid19/current/static/contact-tracing/pdf/ExposureNotification-CryptographySpecificationv1.2.pdf?1.

Contact Tracing Framework Documentation (API); Apple Inc. and Google LLC; Apr. 2020; retrieved from Internet Archive Wayback Machine https://web.archive.org/web/20200410171626/https://covid19-static.cdn-apple.com/applications/covid19/current/static/contact-tracing/pdf/ContactTracing-FrameworkDocumentation.pdf on Jul. 22, 2021.

Stopp Corona; Web page https://participate.roteskreuz.at/stopp-corona/; Mar. 26, 2020; retrieved from Internet Archive Wayback Machine https://web.archive.org/web/20200326073408/https://participate.roteskreuz.at/stopp-corona/ on Jul. 21, 2021.

GitHub—DP-3T; Web page https://github.com/DP-3T/documents; Apr. 3, 2020; retrieved from Internet Archive Wayback Machine https://web.archive.org/web/20200403180921/https://github.com/DP-3T/documents on Jul. 21, 2021.

Decentralized Privacy-Preserving Proximity Tracing; Decentralized Privacy-Preserving Proximity Tracing (DP-3T) project; May 25, 2020 [retrieved on Jul. 21, 2021]; retrieved from the Internet: https://github.com/DP-3T/documents/blob/master/DP3T%20White%20Paper.pdf.

* cited by examiner

ANONYMOUS DISTRIBUTED CONTACT TRACING AND VERIFICATION SYSTEM

CROSS-REFERENCE TO RELATED APPLICATION

The present application is a non-provisional of, and claims priority to, U.S. Provisional Patent Application Ser. No. 62/706,095, filed Jul. 31, 2020, the disclosure of which is incorporated herein by reference in its entirety.

BACKGROUND AND OVERVIEW

The present technology relates to an automated contact tracing system for anonymously identifying contacts between users and a method for operating such a system. Further it is related to a method for operating a server in an automated contact tracing system, a computer program for establishing Encounter-Tokens and a mobile device or wearable device including such a computer program.

Contact tracing is a well-known technique for obtaining information on personal encounters applicable in many different application fields.

One application field may be contact tracing for epidemic control. Many contagious diseases like COVID-19 caused by Corona virus SARS-CoV-2 spread through direct contact between persons. To stop infections from spreading among the population, health authorities have to identify and isolate contacts and whole contact chains of infected persons. Contact tracing currently relies mostly on self-reported information provided by infected persons, resulting in an incomplete list of contacts, as users often cannot remember nor identify all persons that they have recently been in contact with. Moreover, tracing is mainly done manually by the authorities requiring a huge amount of work. This becomes increasingly challenging once the number of infected people becomes high.

Another application field may be a scenario where users want to have a verifiable contact establishment in an automatic and anonymous way. An example of such a use case could be, e.g., participants in a conference, wishing to interact later on, without having to exchange detailed contact information at the time of encounter.

US2017352119 (A1) discloses a system and computing method for tracking the proximity relationships of people via their mobile devices so that such proximity relationships can identify when and where people come into contact with each other. Accordingly, the tracked proximity relationships can provide proximity relationship data. The proximity relationship can be defined by a first person coming into contact with a second person, which can be tracked with a signal tracker. The signal tracker can detect a signal from a signal emitting device, e.g., a mobile device, and when the first person has the signal emitting device in proximity to the signal tracker, the signal tracker can detect and record that the first person was within the proximity of the signal tracker. The signal tracking range of the signal tracker may be used to define a proximity zone of the signal emitting device to the signal tracker, where degrees of proximity can be degrees of closeness to the signal tracker, and thereby each signal tracker can have multiple proximity zones as concentric zones having the signal tracker at substantially the center for each zone. When the second person is in a proximity zone at the time the first person is in the same proximity zone, the first person and second person are defined to have a proximity relationship. The system operates with people that have mobile computing devices (MCDs) that emit one or more types of signals that can be detected by the one or more signal detectors of the signal trackers. The signal tracker receives proximity data from the MCDs and transmits some or all of the proximity data to a server computing system.

A number of other tracing approaches based on exchanging information over proximity communications have been proposed.

The Exposure Notification API by Apple and Google has significant weaknesses in terms of privacy properties. It is based on frequently-changing random pseudonyms, so called Rolling Proximity Identifiers (RPI). In this approach each Tracing App generates these RPIs from a Daily Tracing Key (DTK) and beacons them into their surroundings using Bluetooth LE. Apps on other devices in close proximity can observe these RPIs and sore them locally as a record of contact with the device beaconing the RPI. This dataset also includes additional metadata like the received signal strength. Should a user be tested positive for COVID-19, that user's app uploads DTKs of the last x days to a central server (currently x=14). The server accumulates the received DTKs of infected persons and offers them to be downloaded by other users' apps. Tracing Apps of other users regularly check the server for updates and download any new DTKs. Each app then uses the downloaded DTKs to calculate the corresponding RPI pseudonyms used by the infected persons' apps in the recent past. The operating system/corresponding system service then compares these infected persons' RPIs to the RPIs stored locally on the device. If matching RPIs are found, the metadata, e.g., signal strength or duration of the encounters, related to these matching RPIs are used to calculate a risk score that is used to determine whether a warning should be displayed to the user or not. The Apple and Google approach is thus vulnerable to user profiling attacks. An attacker who observes the RPIs beaconed in a specific area and records them will be able to match its observations with the published RPIs of infected persons and can thus create a movement profile of the person in question.

The Contact tracing framework DP-3T (design 2) is also based on frequently-changing pseudonymous identifiers, so-called Ephemeral IDs that Tracing Apps beacon into their surroundings. Tracing Apps record any Ephemeral IDs they observe for later determination of contacts. Infected users upload their Ephemeral IDs to the Tracing Server, who distributes these to other users. Other user's Tracing Apps download the published Ephemeral IDs and compare them with the Ephemeral IDs they have observed earlier and stored locally. This design is not vulnerable to the profiling attack to the degree that the Apple and Google proposal is, as the published Ephemeral IDs can't be linked to each other. However, this approach is vulnerable to so called relay attacks. In such attacks, the attacker records Ephemeral IDs at place A and transfers and rebroadcasts them to a remote location B. The goal of the attacker is to sabotage the tracing system by creating fake contacts between users. Also, the Apple and Google approach is vulnerable to this attack.

The Austrian StoppCorona Contact Tracing App is also based on exchanging public keys between Tracing Apps. However, the exchange of the public keys happens with the help of a cloud service, from which individual public keys are downloaded. When two Tracing Apps have an encounter, they determine co-presence in proximity using the Google Here service or a similar service called p2pKit. The Tracing Apps then download using the cloud service the public key of the counterpart to their device. The public key-private key pair of each Tracing App remains the same all the time.

When a user is infected with the disease, his Tracing App will encrypt messages with a warning using the public keys of Tracing Apps it has encountered and upload these encrypted messages to the Tracing Server. All other Tracing Apps will download these messages and attempt to decrypt them using their private key. If the decryption succeeds, this is an indication that a contact with an infected person has taken place and the Tracing App can warn its user. The Austrian solution suffers from vulnerability to user tracking. As the cloud service is involved in all exchanges of public keys, the cloud service will be able to track all encounters between users, severely impacting the privacy of the user. On one hand, as the public key of users is static, user movement profiling is also possible by observing the public keys that Tracing Apps transmit in different locations.

SUMMARY OF THE INVENTION

The present invention has been made in view of the above prior art and aims to overcome the technical problems thereof. In particular it is thought to provide a solution with improved privacy options for the user. Further, a respective computer program, a so-called app, for affordable mobile or wearable devices should be provided.

Embodiments of the present invention include an automated contact tracing system for anonymously identifying contacts between users, a method for operating an automated contact tracing system for anonymously identifying contacts between users, a method for operating a server in an automated contact tracing system for anonymously identifying contacts between users, and/or a computer program for establishing Encounter-Tokens with a short-range proximity communication protocol.

The present invention overcomes the technical problems of the known prior art. In particular it provides a solution with improved privacy options for the user. Further, a respective app for affordable mobile or wearable devices is provided.

The present invention does not allow a similar profiling attack as with the Exposure Notification API by Apple and Google, since the Tracing App of an infected person may be programed to upload only such Encounter Tokens to the Tracing Server that have a long enough duration (e.g., 10 minutes) that is relevant for the transmission of the disease.

Further, the present invention is more resilient to relay attacks than the Contact tracing framework DP-3T. For creating fake Encounter Tokens it is not sufficient to relay cryptographic tokens from A to B and rebroadcast them there. The adversary would need to also record cryptographic tokens at location B and rebroadcast them at A for the attack to succeed.

The automated contact tracing system according to the present invention is able to anonymously identify contacts between persons. In this system, human users use a tracing app installed on their mobile device, e.g. a smart phone or even more preferred an affordable wrist band, to establish with the help of a short-range proximity communication protocol like, e.g., Bluetooth Low Energy (Bluetooth LE) so-called Encounter Tokens, when they spend a specific amount of time in close proximity. Other possible communication protocols are WiFi®, Bluetooth®, cellular signals, RFID or tire pressure monitoring signals (TPMS), and other types of signals. Each mobile device has preferably the ability to transmit and/or to receive signals to/from another mobile device. Further, each mobile device has preferably the ability to transmit and/or to receive signals to/from a tracing server. This tracing server can be an individual server, a server array, a distributed server, etc. The close proximity range is defined by the respective needs and could be less than 10 meters, preferable less than 8 meters, more preferable less than 5 meters and most preferable less than 2 meters. An additional factor which can also be stored in the metadata of the encounter token is the duration of the encounter which is preferably more than 2 minutes, preferably more than 10 minutes and more preferably more than 20 minutes and most preferably more than 30 minutes.

In one embodiment of the invention, the system allows app users that are infected with a contagious disease to release and publish with the help of an on-line server system selected Encounter Tokens they have established in order to warn other users that they have been in contact with and thus share an Encounter Token with. Other users can download these Encounter Tokens from the on-line server and cross-check them with the Encounter Tokens they have stored locally. If a matching Encounter Token is found, it is an indication of an encounter with the infected app user. The app can then warn the user that a contact with an infected person has taken place so that the user can take appropriate measures like self-quarantine or seeking a test for determining whether the user has been infected.

In another embodiment of the invention, the Encounter Token can be used as an anonymously verified contact identifier, e.g., for enabling verified communications between the encounter participants later on.

In yet another embodiment of the invention, Encounter Tokens can also be used to establish an anonymous group of people, e.g., people participating in an event or visiting a particular place. In some embodiments of this invention, this could be achieved by assigning the cryptographic tokens used for establishing Encounter Tokens not to individual Tracing Apps, but to groups of Tracing Apps. The established Encounter Tokens would thus be specific to that group and not individual persons.

Furthermore, another embodiment of this invention could use the Encounter Token as an encryption key to encrypt messages among users or groups of users who have encountered earlier.

The information contained in the metadata of the Encounter Token can be either pre-defined in the Tracing App or may be set by the user. The metadata may include the encounter Token ID of the other user, the distance, duration, time and date of the encounter. It may also include the position data and MAC address of the mobile device if required.

In one embodiment of the invention, random ephemeral cryptographic tokens are sent and received over the proximity communication protocol by using smart phones. In other embodiment of the invention, any wearable devices like wristbands also can be used to exchange the tokens because in many use-cases smart phones are not convenient or even not allowed to be used, e.g., sport activities, child users, or many hospitals. Further, such affordable wristbands may be distributed by health authorities free of charge to allow maximum use of the automated contact tracing system for anonymously identifying contacts between users. Likewise, such wristbands may also be used as giveaways for conference participants in other tracing scenarios. Other possible examples are hosting organizations of events, school or university officials, entities running office facilities, or similar entities.

The present invention could be used for:
Pandemic response as a contact tracing system for tracking the infection chains of viral infection diseases like COVID-19; or any other health or disaster specific tracking system; or
Direct, verifiable, and private contact establishment and messaging services with various applications, e.g. evaluation of encounters of personnel which was exposed to radiation.

The invention is commercially applicable, e.g. by a service provider operating tracing servers, providing web apps, mobile apps, APIs (for wearable devices), plug-ins, or library that can be integrated into other third-party apps, dashboards, statistics, and data analysis, messaging.

The autonomous, anonymous, decentralized, and privacy-preserving contact tracing system could also be used for:
Encounter-based direct, verifiable, and private contact establishment and messaging services
Encounter-based statistic services
Centralized or decentralized, anonymous or identified systems defense on use cases.

BRIEF DESCRIPTION OF THE DRAWINGS

In order to best describe the manner in which the above-described embodiments are implemented, as well as define other advantages and features of the disclosure, a more particular description is provided below and is illustrated in the appended drawings. Understanding that these drawings depict only exemplary embodiments of the invention and are not therefore to be considered to be limiting in scope, the examples will be described and explained with additional specificity and detail through the use of the accompanying drawings in which.

DETAILED DESCRIPTION

Various embodiments of the disclosed system and methods are discussed in detail below. While specific implementations are discussed, it should be understood that this is done for illustration purposes only. A person skilled in the relevant art will recognize that other components, configurations, and steps may be used without departing from the spirit and scope of the disclosure.

Figure 1A:
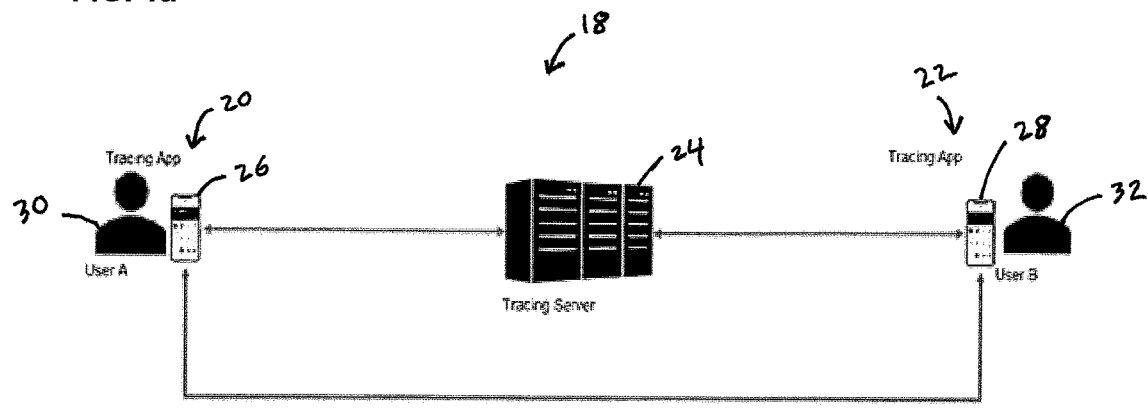
FIG. 1a illustrates a System overview, according to an embodiment of the invention.

FIG. 1a shows a system overview for an embodiment of the present invention. The system 18 comprises two main components, namely respective Tracing apps 20, 22 and a Tracing server 24. The tracing app 20, 22 are installed on respective mobile devices 26, 28 of the user A 30 and user B 32. The mobile devices 26, 28 communicate through a short-range proximity communication protocol with each other. Further, each mobile device 26, 28 of user A 30 and user B 32 communicates with a tracing server 24.

Figure 1B:
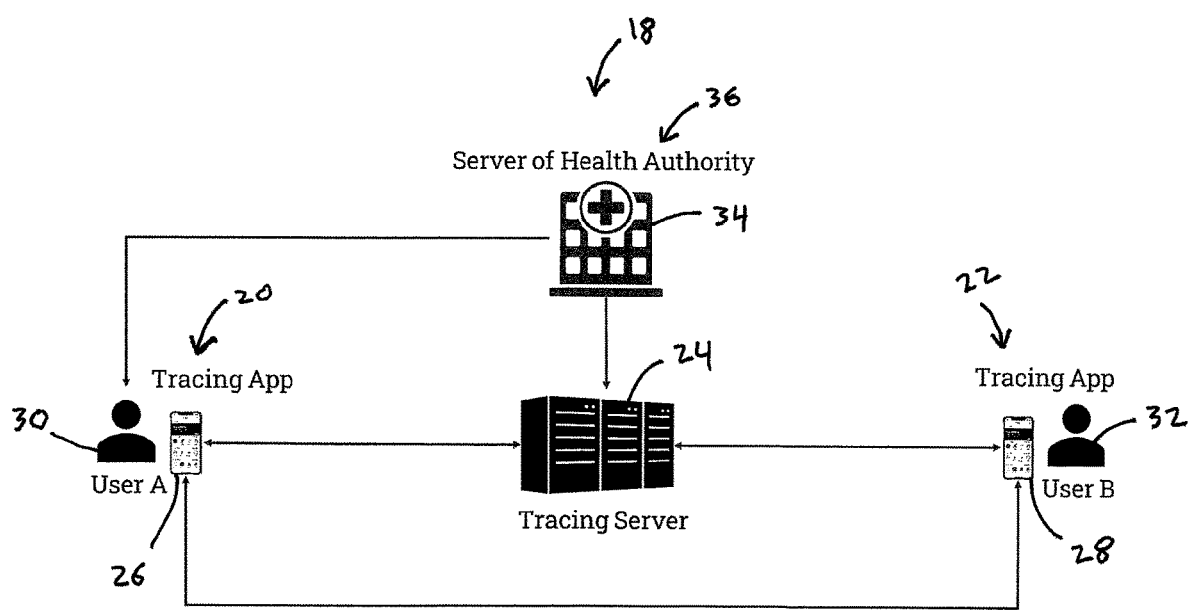
FIG. 1b illustrates a System overview including a server of a Health Authority, according to an embodiment of the invention.

FIG. 1b illustrates another embodiment including a server 34 of a Health Authority 36. This server 34 is connected to a user A 30 which has been infected and with the tracing server 24, to allow the tracing server to communicate the risk of infection due to prior contact with an infected person to user B 32 who had an encounter with user A 30.

The operation of the system 18 of FIG. 1a and FIG. 1b may comprise the following steps:
1. Establishing encounter tokens;
2. Optional verification of infected users if used in an epidemiological context;
3. Encounter token upload to a tracing server;
4. Encounter token download from a tracing server and contact verification;
5. Optional sharing of contact data for epidemiologic research if accepted by the user.

For establishing Encounter Tokens, the Tracing App 20, 22 of a user 30, 32 uses a proximity communication protocol with limited range to sense the presence of tracing Apps from other users 30, 32. In one embodiment of the invention, the used proximity communication protocol could be Bluetooth Low Energy. In other embodiments of the invention, other proximity communication protocols like ZigBee®, Z-Wave® or similar protocols can be used. Each generates a random ephemeral cryptographic token and advertises this over the proximity communication protocol. Tracing Apps 20, 22 on devices of other users 30, 32 in the proximity sense these tokens and store them locally on the mobile device 26, 28 of the other user 30, 32 for further processing.

In one embodiment of the invention, this cryptographic token contains a randomly-generated ephemeral public key associated with the Tracing App 20, 22 of a user 30, 32. In another particular embodiment of this invention, the ephemeral public key is an Elliptic Curve public key. The cryptographic token advertised by the Tracing App 20, 22 of a user 30, 32 must be changed frequently to thwart tracing attacks against the tracing app of the user. In one embodiment of the invention, the cryptographic token is changed every 30 minutes.

Each Tracing App 20, 22 of a user 30, 32 continuously advertises its cryptographic token that is currently valid and records any other cryptographic token generated and sent by a tracing app 20, 22 of another user 30, 32 it can sense in a pre-defined proximity. When the tracing App 20, 22 of a user 30, 32 detects a cryptographic token emitted by a Tracing App 20, 22 of another user 30, 32, it will store the detected token locally and perform an Encounter Token derivation function to derive an Encounter Token for the encounter with the other user 30, 32.

When a mobile device 26, 28 finds another mobile device 26, 28 the two devices start the Ephemeral Cryptographic Token Exchange. First, one device 26, 28 starts the Bluetooth client and the another device 26, 28 starts the Bluetooth server and both devices exchange their Cryptographic Tokens (CTs) (520-bit length). Both devices 26, 28 store the CTs which later on are used to calculate encounter tokens (ET). CT may be changed every 30 minutes along with Ephemeral Identifier (EID). During a 30-minute lifetime, to save energy, CT may only be sent when the device 26, 28 finds a new device 26, 28.

At least the following data items are given as input to the Encounter Token derivation function: the received cryptographic token of the Tracing App 20, 22 of the other user 30, 32 and the generated cryptographic token of the own Tracing App 20, 22 that was valid at the time when the other cryptographic token was received. Based on these inputs, an Encounter Token is calculated by the Encounter Token derivation function.

Figure 1C:
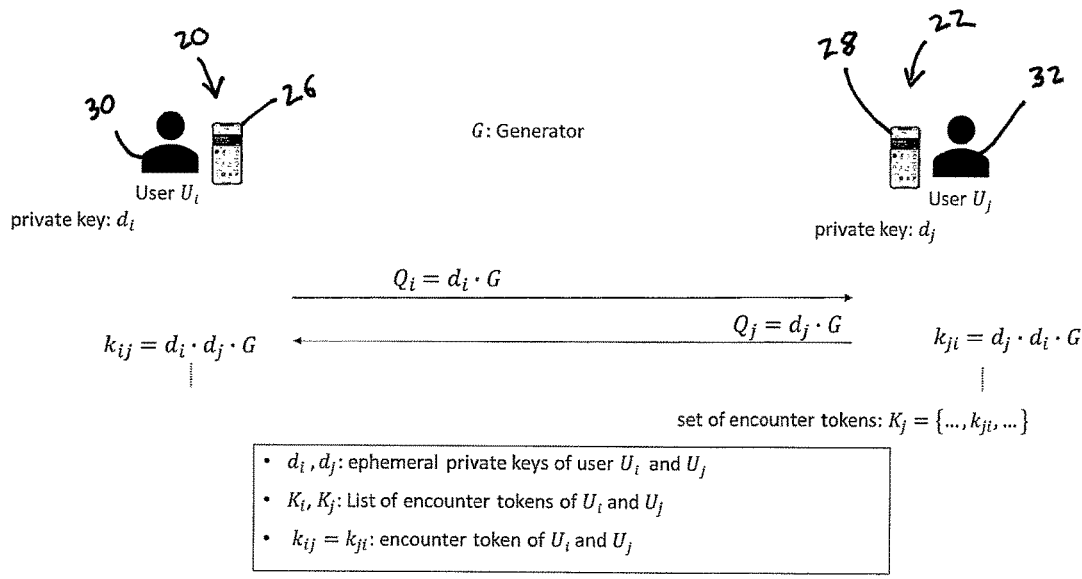
FIG. 1c illustrates an Encounter Token establishment, according to an embodiment of the invention.

In one embodiment of this invention, shown in FIG. 1c, the Encounter Token derivation function performs a known Elliptic Curve Diffie-Hellman (ECDH) key exchange algorithm, in which the Encounter Token is a session key established using the cryptographic tokens representing the public keys of the corresponding Tracing Apps 20, 22.

In another embodiment of the invention, the Diffie-Hellman key exchange algorithm is used. In yet another embodiment of the invention, also a symmetric key agreement protocol can be used.

In yet another embodiment of the invention, the encounter derivation function may be a simple exclusive or operation (XOR) applied on the cryptographic tokens (CT).

In one embodiment of the invention, the cryptographic token generation function and the Encounter Token derivation function are executed during the time when the mobile device 26, 28 is being charged, e.g., during the night, in order to preserve battery lifetime of the mobile device.

Each Tracing App 20, 22 stores the derived Encounter Tokens locally together with metadata characterizing the encounter. In one embodiment of the invention, the metadata comprises at least following data items: duration of the encounter, signal strengths associated with the encounter as well as other contextual information about the encounter. In another embodiment of the invention, the app will also store the location of the encounter as metadata.

In order to make sure that only users who really have been infected can report their Encounter Tokens, the system must verify the infection status of the user 30, 32 submitting their Encounter Tokens to the Tracing Server 24 (FIG. 1b). This can be done in a number of ways.

Figure 2:
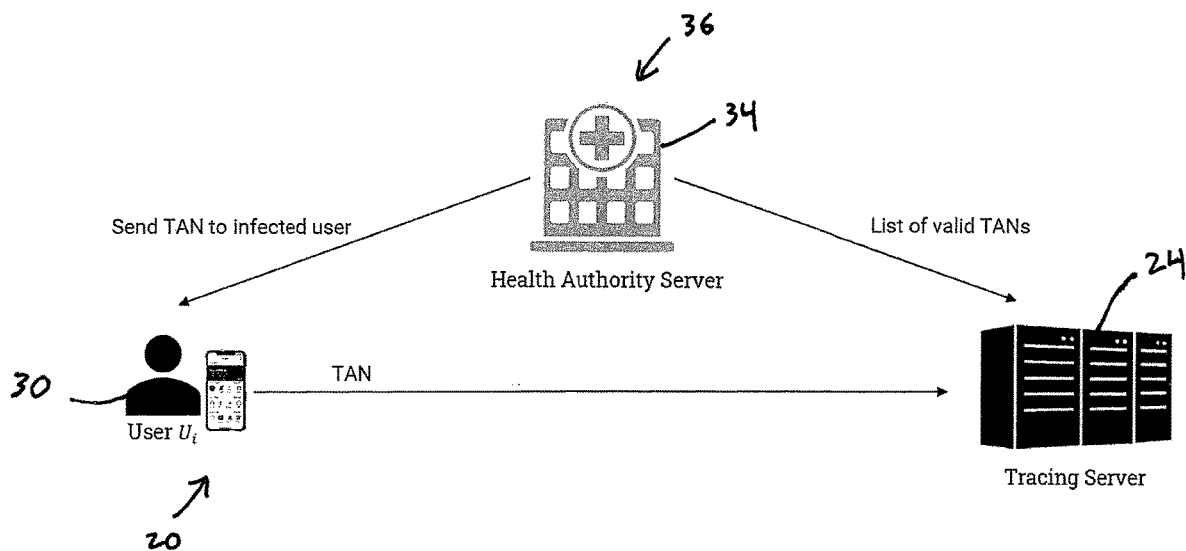
FIG. 2 illustrates an infection status verification, according to an embodiment of the invention.

In one embodiment of the invention, as shown in FIG. 2, a Health Authority Server 34 will issue an authentication code auth-code to a user 30 who has been tested positive for the disease. To verify his infection status the user 30 will enter this authentication code auth-code into the Tracing App 20. The Tracing App 20 will then use the authentication code auth-code for deriving an authenticator value auth-val when uploading Encounter Tokens to the Tracing Server 24. In another embodiment of the invention, the Tracing App 20 derives the authenticator value auth-val using the authentication code auth-code and other metadata like a date, a timestamp or a location code.

In yet another embodiment of the invention, the authentication code auth-code can be given in the form of a QR code printed on paper or transmitted as a PDF file by e-mail. The user 30 may then use the Tracing App QR code reader functionality to photograph the QR code. The Tracing App 20 will then extract the auth-code contained in the QR code.

Encounter Token upload.

The user 30 will enter the authentication code auth-code into its app 20 when uploading the Encounter Tokens (ET) to the Tracing Server 24. The Health Authority Server 34 will send the list of valid auth-codes issued to infected users to the Tracing Server 24.

In one embodiment of the invention, the Tracing App 20 sends the authentication code auth-code to the Tracing Server 24. The Tracing Server 24 will check whether the auth-code received from the Tracing App 20 is among the list of valid auth-codes received from the Health Authority Server 34 and respond with a nonce (random number, used once).

The Tracing App 20 will then derive an authenticator value auth-val and attach it to the message containing the Encounter Tokens it uploads to the Tracing Server 24. The auth-val is a cryptographic message authentication code (MAC) derived from the Encounter Tokens using the authentication code auth-code as the key to the authentication code: auth-val=MAC(auth-code|ET_1|ET_2| . . . |ET_k). In one embodiment of the invention, the nonce received from the Tracing Server 24 is used as the key to the MAC: auth-val=MAC(nonce, |ET_1|ET_2| . . . |ET_k).

In yet another embodiment of the invention, the auth-val also depends on metadata related to the Encounter Tokens: auth-val=MAC(auth-code, metadata, ET_1 ET_2 . . . ET_k), or, auth-val=MAC(nonce, metadata, |ET_1|ET_2| . . . |ET_k).

When the Tracing App 20 sends its Encounter Tokens to the Tracing Server 24, the Tracing Server will check the authenticator value auth-val by calculating if it is derived using a valid auth-code or nonce. If the authenticator value is valid, the submitted Encounter Tokens are accepted and stored locally by the Tracing Server 24. Otherwise they are rejected and discarded.

Figure 3:
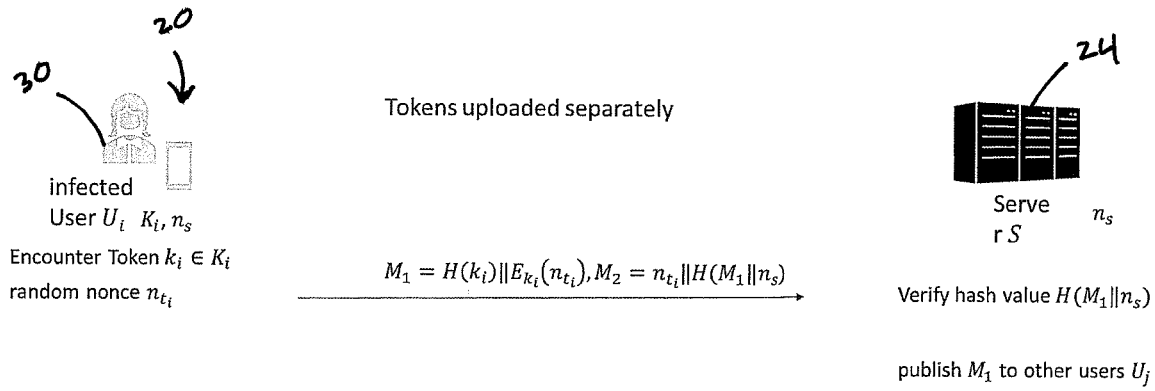
FIG. 3 illustrates an Encounter Token upload, according to an embodiment of the invention.

In another embodiment of the invention shown in FIG. 3, the Tracing App 20 sends an authentication code auth-code to the Tracing Server 24 and receives a list of nonces (n_1, n_2, . . . , n_k) from the Tracing Server 24. The Tracing App 20 then calculates an authentication value auth-val_i for each Encounter Token ET_i separately: auth-val_1=MAC (n_1|ET_1), auth-val_2=MAC(n_2|ET_2), . . . , auth-val_k=MAC(n_k|ET_k). The Tracing Server 24 will then check each Encounter Token ET_i separately by verifying that its authenticator value auth-val_i is derived using a valid nonce n_i.

In a preferred embodiment of this invention the Encounter Tokens (ET) are not transmitted to the Tracing Server 24 in plain text, but instead a cryptographic hash value h(ET) of the Encounter Token is transmitted instead of the Encounter Token.

In a preferred embodiment of the invention, the Tracing App 20 will upload only such Encounter Tokens that have a duration associated with them that exceeds a minimum duration threshold (e.g., 10 minutes). This is to avoid publishing unnecessary information that is not relevant for the transmission of the disease and thus protect the user's privacy.

Figure 4:
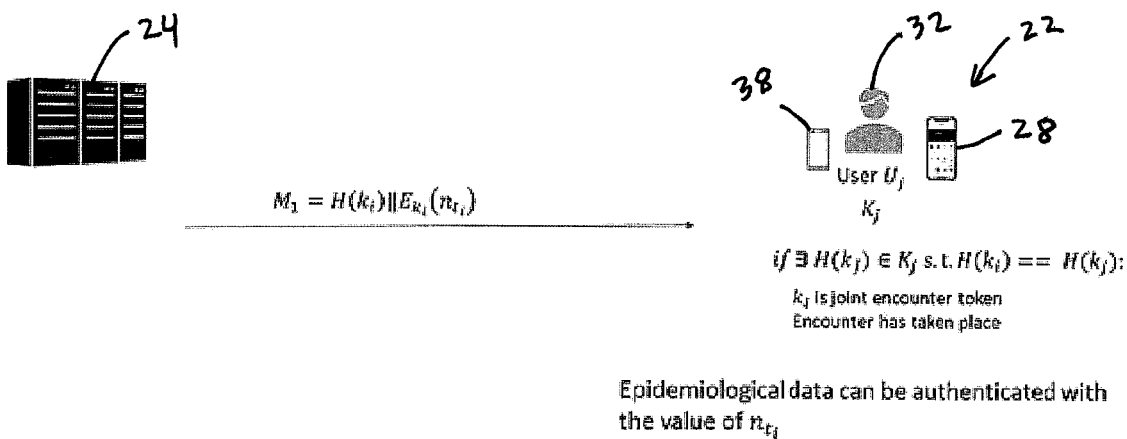
FIG. 4 illustrates an Encounter Token download and contact verification, according to an embodiment of the invention.

FIG. 4 illustrates the Encounter Token download and contact verification. Each Tracing App 22 participating in the system may regularly download verified Encounter Tokens ET from the Tracing Server 24. In a preferred embodiment of this invention, the download will take place at least once a day. In another embodiment, the time of the download is determined based on a random time interval within maximum interval duration.

The Tracing App 22 will download a list (ET_1, ET_2, . . . , ET_k) of Encounter Tokens. It will then compare each of these Encounter Tokens to the list of Encounter Tokens stored locally on the mobile device. If a matching ET_i is found, the Tracing App 22 will notify the user 32 that an encounter with a person tested positive with the infectious disease. In another embodiment of the invention, also other suitable actions can be triggered by the Tracing App 22, including, e.g., establishing contact or communications with health authorities.

In another embodiment of the invention, upon a matching Encounter Token is found, additional metadata stored with the Encounter Token may be examined to determine an infection risk level.

In yet another embodiment, the notification of the contact with an infected person may be triggered by the Tracing App 22 only if the determined risk level surpasses a determined threshold value.

In yet another embodiment, the actions taken by the Tracing App 22 may be dependent on the determined risk level.

In a preferred embodiment of the invention the matching of Encounter Tokens is based on the cryptographic hash values h(ET) of the Encounter Tokens (ET).

In one embodiment of the invention, the Tracing App 22 can be used to share information about verified encounters with an external entity. An external entity could be, e.g., an epidemiological research institute 36 (FIG. 2). In this embodiment, the Tracing App 20 (FIG. 3) of the infected person 30 (FIG. 3) attaches to each Encounter Token ET_i an individual encrypted nonce value enc-n_i, using the encounter token ET_i as the encryption key: enc-n_i=encryption(ET n_i). In this embodiment, only cryptographic hash values of the Encounter Tokens are sent to the Tracing Server 24.

In this embodiment, other Tracing Apps will retrieve the verified cryptographic hash values h(ET_i) as well as the encrypted Encounter Token-specific nonce values enc-n_i from the Tracing Server 24. The Tracing Apps 22 compare the cryptographic hashes with the cryptographic hashes of their own Encounter Tokens and if a match is determined, they use the value of the matching Encounter Token ET_i to decrypt the nonce value n_i: n_i=decryption(ET_i, enc-n_i).

In one particular embodiment of this invention, the encryption algorithm AES is used for encryption and decryption.

In the preferred embodiment of this invention, the Tracing App 20 (FIG. 3) of the infected person 30 (FIG. 3) receives the Encounter Token-specific nonces n_i used from the Tracing Server 24. In another embodiment, the Tracing App 20 (FIG. 3) of the infected person 30 (FIG. 3) generates the Encounter Token-specific nonces itself and provides the list of nonces to the Tracing Server 24 when it uploads its Encounter Tokens to the Tracing Server.

For allowing an external entity 36 (FIG. 2) to verify contacts to infected persons, the Tracing Server 24 will share the list of Encounter Token-specific nonces with the external entity. When a Tracing App 22 determines that a contact with an infected person has taken place, it will use the matching Encounter Token as described above to decrypt the nonce associated with the matching Encounter Token and can send this nonce to the external entity 36 (FIG. 2). If the nonce is on the list of nonces provided to the external entity by the Tracing Server 24, the nonce is a valid proof of a contact with an infected person.

In one embodiment of the invention the external entity 36 (FIG. 2) will keep track of nonces provided to it as proof of contact and accept only one instance of each nonce in order to make it impossible for malicious Tracing Apps to duplicate proofs of contact by sending decrypted nonce.

In one embodiment of the invention, the proximity communication required for exchange of the cryptographic tokens is realized by an external wearable device 38. Wearable devices 38 can be wristbands, bracelets, necklaces, jewelry, etc. with built in processing capability, memory and proximity communication interfaces for communicating with other Tracing Apps or wearables. The main advantage of this embodiment is that the tracing functionality is not tied to the possession of a smart phone, but can also be used in usage contexts where using or carrying a smart phone is inconvenient or not possible. Examples of such usage contexts include sports activities, children at school or the playground and other comparable situations, in which one cannot assume users to constantly carry a smart phone with them. Carrying a wristband, on the other hand, is not intrusive and can be used in most situations, e.g., even under the shower, as wristbands usually are water-proof, contrary to many smart phone models.

In this embodiment, the wearable device 38 is paired with the user's tracing app 22 and communicates over the proximity communication protocol with the Tracing App. The Tracing App 22 generates cryptographic tokens used for Encounter Token establishment and uploads them over the proximity communication channel to the wearable 38. The wearable 38 will store the cryptographic tokens locally.

According to a fixed time schedule, the wearable device 38 will transmit the cryptographic tokens into its proximity over the proximity communication protocol. The wearable device 38 exchanges cryptographic tokens with other devices in proximity and stores cryptographic tokens of other devices it encounters locally. The wearable device 38 and the smart phone 28 frequently synchronize their data, so that the smart phone sends the cryptographic tokens that it generates to the wearable device and the wearable device sends the cryptographic tokens it has stored locally along with metadata associated with them to the smart phone. This synchronization function can be executed periodically or when the phone is charged or when the user interacts with the Tracing App 22, i.e., the app is running in the foreground.

The role of the wristband could be to exchange the cryptographic tokens required for establishing Encounter Tokens and transmit these to the Tracing App 22 with which it is paired. The derivation of Encounter Tokens, uploading Encounter Tokens to the Tracing Server 24, as well as downloading Encounter Tokens and contact verification all are performed by the Tracing App 22 independent of the wearable device 38. The tracing app 22 could be installed on a smart phone, a PC computer or any other suitable device to be connected to the wrist band and the tracing server 24.

The uploading and downloading of information can be in real time or subsequently, depending of the needs and the nature of the used device.

The number of expected encounter tokens is relevant for the size of the data storage to be provided by the mobile device 28. In average, a user has ca. 20 encounters (15 minutes or longer) with other users excluding known contacts e.g., household members or colleagues in the same office. Therefore, the expected number of Encounter Tokens per day is 20 Encounter tokens, preferably 30 Encounter tokens, more preferable 50 encounter tokens per day.

The app 20 (FIG. 3) of the infected user 30 (FIG. 3) uploads the hashes (128 bits) of Encounter Tokens (ETs) for 14 days. Hence, the total amount of data uploaded by the app 20 (FIG. 3) to the server 24 can be estimated to be, 14 days*20encounter tokens*128 bits=35,840 (bits) or 4.3 (kB). In case of higher numbers of encounter tokens this amount of data will increase respectively.

Under the assumption that there are 2000 new COVID-19 cases per day, the tracing app 22 according to an embodiment of the present invention will download from the tracing server 2000 cases*4.3 kB=8,600 (kB) or 8.6 MB per day. Also here, the amount of data will vary depending on the assumed numbers of cases and the amount of uploaded data.

Assuming that there are 2000 new COVID-19 cases per day, the tracing server 24 will receive 2000cases*4.3 kB=8, 600 (kB) or 8.6 MB per day (the same to the data that an app downloaded).

Further assuming that there are 50 million app users, the tracing server 24 will send 50,000,000 users*8.6 MB=430,000,000 (MB) or 430 TB per day. If the number of users is higher, the numbers have to be adapted accordingly and the capacity of the tracing server will need to match these numbers.

In order to establish an Encounter Token (ET), the mobile device 28 needs to send and receive an advertising message (AM) and cryptographic token (CT) that are 192+520=712 (bits) or 712*2=1,424 (bits) for both sending and receiving. In the worst case, the BLE bandwidth is 125 (kbit/s) that means the tracing app 22 can establish 125,000/1,424=175 ETs per second. In the ideal case, the BLE bandwidth is 2 Mbit/s that means the tracing app 22 can establish 2,000,000/1,424=1,404 ETs per second. However, since the latency to establish a BLE connection is ca. 6 ms, the tracing app 22 may only establish 1000/6=160 ETs per second assuming that the data transmission time is much smaller than the connection time, it is fair to estimate that the tracing app 22 can establish 100 encounters per second, i.e. the maximum numbers of devices in a pre-defined proximity that the App 22 can establish the Encounter Tokens for is approximately 100/sec.

According to one embodiment of the present invention, the tracing app 22 constantly advertises and scans for advertising messages (AMs). The tracing app 22 periodically advertises AMs for every minute, in which devices run BLE advertising for 40 seconds and are in idle mode for 20 seconds. The tracing app 22 periodically scans AMs for every 50 seconds, in which devices run BLE scanning for 30 seconds and are in idle mode for 20 seconds. These advertising and scanning patterns are empirically selected to ensure that the tracing app 22 keeps track of other devices every 2 minutes.

According to one aspect of the invention no position data are provided in the metadata of the encounter token. This increases the privacy of the user and is not necessary for the evaluation of an infection risk. However, in other embodiments, the position data may be included in the metadata of the encounter token.

Those of skill in the art will appreciate that other embodiments of the invention may be practiced in an automated contact tracing system for anonymously identifying contacts between users. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Communication at various stages of the described system can be performed through a variety of communication protocols. Although the underlying communication technology may change, the fundamental principles described herein are still applicable.

The various embodiments described above are provided by way of illustration only and should not be construed to limit the invention. For example, the principles herein may be applied to any mobile device or tag. Those skilled in the art will readily recognize various modifications and changes that may be made to the present invention, without following the example embodiments and applications illustrated and described herein, by combining only some technical features of different embodiments as far as technical possible, without departing from the scope of the present disclosure.

What is claimed is:

1. An automated contact tracing system for anonymously identifying contacts between users, the system comprising:
   a tracing server comprising at least one memory and one or more processors;
   more than one mobile device or wearable device of a user each comprising at least
   one memory, means for short-range proximity communication, and one or more processors for carrying out a computer program for generating Encounter-Tokens, when the mobile device or wearable device of one user spends a pre-defined amount of time in a pre-defined proximity range of the mobile device or wearable device of another user; and
   a health authority server distinct from and connectable to the tracing server and connectable to the more than one mobile device or wearable device of a user, wherein the health authority server comprises at least one memory and one or more processors, issues authentication codes to users infected with diseases, and sends a list of valid authentication codes issued to infected users to the tracing server;
   wherein, upon receiving an authentication code of a user from a mobile device or wearable device of the user, at least one processor of the one or more processors of the tracing server is configured to:
      verify the infection status of the user by checking that the authentication code of the user is among the list of valid authentication codes received from the health authority server; and
      upon verifying that the authentication code of the user is among the list of valid authentication codes received from the health authority server, generate and send one or more nonces to the mobile device or wearable device of the user; and
   wherein the computer program of the mobile device or wearable device of the user comprises instructions which, when the computer program is executed by at least one processor of the one or more processors for carrying out the computer program, cause the at least one processor of the one or more processors for carrying out the computer program to:
      upon receipt of the one or more nonces from the tracing server by the mobile device or wearable device of the user, derive one or more authenticator values, each of which comprises a cryptographic message authentication code (MAC), from one or more Encounter Tokens generated by the computer program using the authentication code or a nonce of the one or more nonces as a key to the cryptographic MAC;
      upload one or more Encounter-Tokens generated by the computer program to the tracing server with the one or more authenticator values;
      download at least one verified Encounter-Token from the tracing server; compare each downloaded verified Encounter-Token to each Encounter-Token
   generated by the computer program and stored in the at least one memory of the mobile device or wearable device of the user; and
      upon finding a match between a downloaded verified Encounter-Token and a generated Encounter-Token, notify the respective user that the respective user had an encounter with another user who tested positive with an infectious disease.

2. A method for operating an automated contact tracing system for anonymously identifying contacts between users comprising a tracing server, a health authority server, and more than one mobile device or wearable device of a user, each of which comprises at least one memory and one or more processors, the method comprising the following steps:
   upon mobile devices or wearable devices of users spending a pre-defined amount
   of time in a pre-defined proximity range of each other, generating Encounter-Tokens using a computer program executed by at least one processor of the one or more processors of the mobile device or wearable device of the users;
      issuing authentication codes to users infected with diseases using the health authority server;
      sending a list of valid authentication codes issued to infected users to the tracing server using the health authority server;
      upon receiving authentication codes of users from mobile devices or wearable devices of the users at the tracing server, using at least one processor of the one or more processors of the tracing server to:
         verify the infection status of the users by checking that the authentication codes are among the list of valid authentication codes received from the health authority server;
         upon verifying that the authentication codes are among the list of valid authentication codes received from the health authority server, generate and send one or more nonces to the mobile devices or wearable devices of the respective users;
      upon receipt of the one or more nonces from the tracing server by the mobile devices or wearable devices of the respective users, using at least one processor of the one or more processors of the mobile devices or wearable devices of the respective users to:
         derive one or more authenticator values, each of which comprises a cryptographic message authentication code (MAC), from one or more Encounter Tokens generated by the computer program using the authentication code or a nonce of the one or more nonces as a key to the cryptographic MAC;
         upload one or more Encounter-Tokens generated by the computer program to the tracing server with the one or more authenticator values;
         download at least one verified Encounter-Token from the tracing server; compare each downloaded verified Encounter-Token to each Encounter-Token
      generated by the computer program and stored in the at least one memory of the mobile devices or wearable devices of the users; and
         upon finding a match between a downloaded verified Encounter-Token and a generated Encounter-Token, notify the respective users that the respective users had an encounter with another user who tested positive with an infectious disease.

3. The method according to claim 2, further comprising:
   storing Encounter-Tokens received at the tracing server for a pre-defined duration; and
   automatically deleting the Encounter-Tokens after a pre-defined duration.

4. The method according to claim 3, further comprising voluntary sharing of contact data between mobile devices or wearable devices of users.

5. The method according to claim 2, further comprising voluntary sharing of contact data between mobile devices or wearable devices of users.

6. The system of claim 1 wherein the instructions which, when the computer program is executed by at least one processor of the one or more processors for carrying out the computer program, cause the at least one processor of the one or more processors for carrying out the computer program to:
   receive a cryptographic token from a Tracing App of another user;
   generate a cryptographic token of the user's Tracing App that was valid at the time when the other cryptographic token was received; and
   calculate an Encounter-Token with an Encounter-Token derivation function.

7. The system of claim 6 wherein the instructions, which when the computer program is executed by at least one processor for carrying out the computer program, cause the at least one processor of the one or more processors for carrying out the computer program to generate a random ephemeral cryptographic token.

8. The system of claim 7 wherein the instructions, which when the computer program is executed by at least one processor of the one or more processors for carrying out the computer program, cause the at least one processor of the one or more processors for carrying out the computer program to advertise the random ephemeral cryptographic token over a proximity communication protocol.

9. The system of claim 6 wherein the instructions, which when the computer program is executed by at least one processor of the one or more processors for carrying out the computer program, cause the at least one processor of the one or more processors for carrying out the computer program to store received cryptographic tokens locally for further processing.

10. The system of claim 7 wherein the instructions, which when the computer program is executed by at least one processor of the one or more processors for carrying out the computer program, cause the at least one processor of the one or more processors for carrying out the computer program to store received cryptographic tokens locally for further processing.

11. The system of claim 8 wherein the instructions, which when the computer program is executed by at least one processor of the one or more processors for carrying out the computer program, cause the at least one processor of the one or more processors for carrying out the computer program to store received cryptographic tokens locally for further processing.

12. The method according to claim 2 wherein each mobile device or wearable device of the users comprises a mobile device or a wearable device comprising means for short-range proximity communication.

13. The system of claim 1 wherein the instructions which, when the computer program is executed by at least one processor of the one or more processors for carrying out the computer program, cause the at least one processor of the one or more processors for carrying out the computer program to:
   determine an infection risk level based on metadata stored with the generated Encounter Token matched to the downloaded verified Encounter-Token; and
   notify the respective user of the infection risk level.

14. The system of claim 1 wherein the instructions, which when the computer program is executed by at least one processor of the one or more processors for carrying out the computer program, cause the at least one processor of the one or more processors for carrying out the computer program to upload the at least one Encounter-Token to the tracing server as a cryptographic hash value of the at least one Encounter-Token.

15. The system of claim 1 wherein:
at least one processor of the one or more processors of the tracing server is configured to generate and send the one or more nonces to the mobile device or wearable device of the user as a list of nonces; and
the instructions, which when the computer program is executed by at least one processor of the one or more processors for carrying out the computer program, cause the at least one processor of the one or more processors for carrying out the computer program to derive the one or more authenticator values as a separate authenticator value for each Encounter-Token using one or more nones from the among the list of nonces as keys to the cryptographic MACs of the separate authenticator valves.

16. The system of claim 1 wherein, upon receiving the one more Encounter-Tokens and one or more authenticator values, at least one processor of the one or more processors of the tracing server is configured to check the one or more authenticator values by calculating if the one or more authenticator values were derived from an authentication code in the list of valid authentication codes received from the health authority server or a nonce of the one or more nonces sent to the mobile device or wearable device of the user.

* * * * *

UNITED STATES PATENT AND TRADEMARK OFFICE
CERTIFICATE OF CORRECTION

PATENT NO. : 12,335,394 B2  
APPLICATION NO. : 17/444090  
DATED : June 17, 2025  
INVENTOR(S) : Miettinen et al.

Page 1 of 1

It is certified that error appears in the above-identified patent and that said Letters Patent is hereby corrected as shown below:

In the Specification

Column 9, Line 19, delete:  
"$n\_i=encryption(ET\ n\_i)$."  
And substitute therefor:  
-- $n\_i=encryption(ET\_i, n\_i)$. --

Signed and Sealed this  
Thirtieth Day of December, 2025

John A. Squires  
*Director of the United States Patent and Trademark Office*